(12) United States Patent
Yukimasa et al.

(10) Patent No.: US 7,267,986 B2
(45) Date of Patent: Sep. 11, 2007

(54) METHOD OF DETECTING INORGANIC PHOSPHORIC ACID, PYROPHOSPHATE AND NUCLEIC ACID, AND METHOD OF TYPING SNP SEQUENCE OF DNA

(75) Inventors: Tetsuo Yukimasa, Nara (JP); Hidenobu Yaku, Kadoma (JP); Kimi Fukahi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 502 days.

(21) Appl. No.: 10/699,848

(22) Filed: Nov. 4, 2003

(65) Prior Publication Data

US 2004/0171100 A1    Sep. 2, 2004

Related U.S. Application Data

(63) Continuation of application No. PCT/JP03/03146, filed on Mar. 17, 2003.

(30) Foreign Application Priority Data

Mar. 19, 2002   (JP) .............................. 2002-077359

(51) Int. Cl.
    *G01N 33/00* (2006.01)
(52) U.S. Cl. ....................................................... 436/34
(58) Field of Classification Search ..................... None
    See application file for complete search history.

(56) References Cited

U.S. PATENT DOCUMENTS

| | | | |
|---|---|---|---|
| 5,032,506 A | | 7/1991 | Palmer et al. |
| 5,849,487 A | | 12/1998 | Hase et al. |
| 6,258,568 B1 | * | 7/2001 | Nyren ....................... 435/91.1 |

FOREIGN PATENT DOCUMENTS

| | | |
|---|---|---|
| EP | 0 665 293 A2 | 1/1995 |
| EP | 1 098 193 A1 | 5/2001 |
| EP | 0 946 752 B1 | 6/2002 |
| JP | 56-35050 | 4/1981 |
| JP | 60-078578 | 5/1985 |
| JP | 63-49100 | 3/1988 |
| JP | 63-74499 | 4/1988 |
| JP | 4-349898 | 12/1992 |
| JP | 6-178698 | 6/1994 |
| JP | 8-116967 | 5/1996 |
| JP | 2000-189188 | 7/2000 |
| WO | WO 92/21776 | 12/1992 |
| WO | WO 99/57321 | 11/1999 |

OTHER PUBLICATIONS

Scopes (1972) Analytical Biochemistry 49: 88-94.*
English translation of Japanese Patent JP Pat. 2000-189188 Imamura, S. and Ikura, Y.*
Baykov and Avaeva (1982) Analytical Biochemistry 119, 211-213.*
Baykov and Avaeva (1981) Analytical Biochemistry 116, 1-4.*
Alvarez-Gonzalez (2000) Anal. Chem. 72: 520-527.*
Gorton and Dominguez (2002) Reviews in Mol. Biotechnol. 82: 371-392.*
Carlier, M-F, "Measurement of Phosphate, Dissociation From Actin Filaments Following ATP Hydrolysis Using a Linked Enzyme Assay", Biochemical and Biophysical Research Communications, vol. 143, No. 3, 1987, pp. 1069-1075, XP009063032 ISSN: 0006-291X.
Guynn, Robert W. et al., "Enzymic Determination of Inorganic Phosphate in the Presence of Creatine Phosphate", Analytical Biochemistry, vol. 45, No. 1, 1972, pp. 277-285, XP009062952.
Gibson, Neil J. et al., "A Colorimetric Assay for Phosphate to Measure Amplicon Accumulation in Polymerase Chain Reaction", vol. 254, No. 1, (Dec. 1, 1997), pp. 18-22, XP007900121, ISSN: 0003-2697.
Nyren, P. et al., "Solid Phase DNA Minisequencing by an Enzymatic Luminometric Inorganic Pyrophosphate Detection Assay", Analytical Biochemistry, Academic Press, vol. 208, No. 1, (Jan. 1993), pp. 171-175, XP000335813, ISSN: 0003-2697.
Hoening, M. et al., "A Microtiter Plate Assay for Inorganic Phosphate", Journal of Biochemical and Biophysical Methods, vol. 19, No. 203, 1989, pp. 249-252, XP007900123, ISSN: 0165-022X.
Tatsuma, T., et al., "Enzyme Monolayer- and Bilayer-Modified Electrodes With Diaphorase and Dehydrogenases", Journal of Electroanalytical Chemistry and Interfacial Electrochemistry, vol. 310, No. 1/2, (1991) pp. 149-157, XP000995069, ISSN: 0022-0728.

* cited by examiner

*Primary Examiner*—Teresa E. Strzelecka
*Assistant Examiner*—Suchira Pande
(74) *Attorney, Agent, or Firm*—McDermott Will & Emery LLP

(57) ABSTRACT

According to the present invention, an inorganic phosphoric acid is detected by a method which includes: subjecting a sample to a measurement system containing glyceraldehyde-3-phosphate, oxidized nicotinamide adenine dinucleotide or oxidized nicotinamide adenine dinucleotide phosphate, glyceraldehyde phosphate dehydrogenase, and an electron mediator; and measuring a current value in the measurement system. In the method, a pyrophosphate is quantitatively measured with high sensitivity and at a high speed through converting the pyrophosphate in a sample into an inorganic phosphoric acid. Such a measurement of a pyrophosphate allows for quantitative determination of the pyrophosphate which is produced concurrent with the extension of a DNA, thereby enabling the detection of the presence of a targeted nucleic acid, and typing of a base in a SNP site of a targeted DNA.

9 Claims, 10 Drawing Sheets

Polymerization reaction

Substitution of chain

Cleavage

Completion of the polymerization reaction

METHOD OF DETECTING INORGANIC PHOSPHORIC ACID, PYROPHOSPHATE AND NUCLEIC ACID, AND METHOD OF TYPING SNP SEQUENCE OF DNA

This is a continuation application under 35 U.S.C. 111(a) of pending prior International Application No. PCT/JP03/03146, filed on Mar. 17, 2003.

BACKGROUND OF THE INVENTION

1. Field of the Invention

The present invention relates to a method of detecting inorganic phosphoric acids or pyrophosphates. Further, the present invention relates to a method of simply detecting a targeted nucleic acid in a sample with high sensitivity through the detection described above, and in particular, a method for discriminating a SNP.

2. Description of the Related Art

In recent years, techniques relating to gene information have been actively developed. In a medical field, therapies of diseases at the molecular level have been enabled by analyses of a gene relating to the disease. Further, tailor made medical cares corresponding to every patient has been also enabled by gene diagnosis. In a pharmaceutical field, protein molecules such as antibodies and hormones have been specified using gene information, and utilized as a medicament. Also in agricultural or food fields, many products in which gene information is utilized have been manufactured.

Among such gene information, genetic polymorphisms are particularly important. Similarly to variations of our faces and body types, considerable part of the gene information also varies each person to person. Among the differences in such gene information, an alteration of the base sequence that is present in a frequency of 1% or greater of the population is referred to as a genetic polymorphism. Such genetic polymorphism is mentioned as relating to causes of various diseases, constitution, drug responsiveness, adverse reactions by drugs, and the like as well as facial appearance of each person. Currently, relationships between the genetic polymorphisms and diseases have been rapidly investigated.

Among the genetic polymorphisms, SNP (Single Nucleotide Polymorphism) has been particularly attracted the attention in recent years. SNP refers to a genetic polymorphism involving a difference in single base alone in the base sequence of gene information. SNP is referred to as existing in human genomic DNA by 2 to 3 million, and is readily utilized as a marker of a genetic polymorphism. Thus, the application thereof to the clinical field has been expected. At present, as related techniques to SNPs, development of typing techniques of SNPs in which a base is discriminated of the SNP site has been performed, in addition to studies on identification of a SNP site in a genome and on relationships between SNPs and diseases, and the like.

In general, as a means to discriminate the difference in a base sequence of a DNA, Sanger's (dideoxy) method, DNA tip method or the like has been used. In Sanger's method, SNP typing is executed through the amplification of a region to be analyzed of a human gene by a PCR (polymerase chain reaction) method followed by sequencing through reading the base sequence of a desired position to directly determine the base sequence. In the DNA tip method, a PCR product of a cDNA or an oligonucleotide probe having 15 to 20 bases is immobilized on a substrate, and thereto is hybridized a sample DNA which had been labeled with fluorescence. By strictly controlling the hybridization condition such as temperature and the like, SNP is detected on the basis of the difference of affinity between a probe and the sample DNA, i.e., by the difference in fluorescent intensities.

Moreover, in an attempt to allow for large scale SNP typing, JP-T (the term "JP-T" as used herein means a published Japanese translation of PCT Patent Application) No. 10-510982 (TaqMan PCR method) and JP-T No. 2001-518805 (Invader method) and the like have been disclosed. Diagrammic illustration of the method disclosed in JP-T No. 10-510982 is shown in FIG. 1. In JP-T No. 10-510982, an oligonucleotide probe is provided which includes a fluorescent molecule and a quencher molecule capable of quenching the fluorescence of the fluorescent molecule. An oligonucleotide probe is used which includes a reporter molecule-quencher molecule pair which is to be specifically annealed in a "downstream region" (i.e., in an extending direction of the primer binding site) of a target polynucleotide. These quencher molecule and reporter molecule are arranged close enough with each other. Accordingly, when the reporter molecule is thereby excited, this excitation state energy is constantly transmitted to the quencher molecule in a non-radioactive fashion. Thus, the energy is quenched in a nonradioactive fashion, or emitted at the frequency which is different from the luminescent frequency of the reporter molecule. The probe is annealed with a template during the chain extension by DNA polymerase, and this probe is then digested by 5'→3' exonuclease of the polymerase. As a consequence of digestion of the probe, this reporter molecule is effectively separated from the quencher molecule. Accordingly, the quencher molecule can no longer get close enough to the reporter molecule such that it can quench the fluorescence of the reporter molecule. Therefore, the more the probe is digested upon amplification, number of the reporter molecules in the solution is increased, resulting in increase of number of nonquenching reporter molecules, thereby the fluorescent signal increasingly enhanced.

JP-T No. 2001-518805 discloses a method of detecting the presence of a target nucleic acid molecule. Diagrammic illustration of this method is shown in FIG. 2. A method is disclosed which comprises providing: a structure-specific nuclease, a source of a first target nucleic acid, said first target nucleic acid having a first region, a second region and a third region, wherein said first region is located adjacent to and downstream from said second region and wherein said second region is located adjacent to and downstream from said third region; a first oligonucleotide having a 5' portion and a 3' portion wherein said 5' portion of said first oligonucleotide contains a sequence complementary to said second region of said first target nucleic acid and wherein said 3' portion of said first oligonucleotide contains a sequence complementary to said third region of said first target nucleic acid; a second oligonucleotide having a 5' portion and a 3' portion wherein said 5' portion of said second oligonucleotide contains a sequence complementary to said first region of said first target nucleic acid and wherein said 3' portion of said second oligonucleotide contains a sequence complementary to said second region of said first target nucleic acid; a source of a second target nucleic acid, said second target nucleic acid having a first region, a second region and a third region, wherein said first region is located adjacent to and downstream from said second region and wherein said second region is located adjacent to and downstream from said third region; a third oligonucleotide having a 5' portion and a 3' portion wherein said 5' portion of said third oligonucleotide contains a sequence complementary to said second region of said second target nucleic acid and wherein said 3' portion of said third oligonucleotide contains a sequence complementary to said third region of said second target nucleic acid; generating a first cleavage structure wherein at least said 3' portion of said first oligonucleotide is annealed to said first target nucleic acid and wherein at least 5' portion of said second oligonucleotide is annealed to said first target nucleic acid and wherein cleavage of said first cleavage structure occurs via said structure-specific nuclease thereby cleaving said first oligonucleotide to generate a fourth oligonucleotide, said fourth oligonucleotide having a 5' portion and a 3' portion wherein said 5' portion of said fourth oligonucleotide contains a sequence complementary to said first region of said second target nucleic acid and wherein said 3' portion of said fourth oligonucleotide contains a sequence complementary to said second region of said second target nucleic acid; generating a second cleavage structure wherein at least said 3' portion of said third oligonucleotide is annealed to said second target nucleic acid and wherein at least said 5' portion of said fourth oligonucleotide is annealed to said second target nucleic acid and wherein cleavage of said second cleavage structure occurs to generate a fifth oligonucleotide, said fifth oligonucleotide having a 3' hydroxyl group; and detecting said fifth oligonucleotide.

However, any of these methods uses fluorescent labeling for the probe, therefore, reagents and the like become very expensive, and a light source for laser irradiation or the like is required for detecting fluorescence, leading to size enlargement of the equipment for the measurement. Accordingly, there still exist many problems taking into account of the use for clinical applications in medical institutions.

To the contrary, as a new method of determining a DNA base sequence, JP-T No. 2001-506864 discloses a method in which a pyrophosphate, which is generated concurrent with an extension reaction of a DNA is converted into ATP (adenosine triphosphate), and luminescence by luciferin is detected on the basis of the action of luciferase using the ATP as a substrate. Diagrammic illustration of this method is shown in FIG. 3. Provided is method wherein an extension primer, which hybridizes to a sample DNA immediately adjacent to the target position is provided and the sample DNA and extension primer are subjected to a polymerase reaction in the presence of a deoxynucleotide or dideoxynucleotide whereby the deoxynucleotide or dideoxynucleotide will only become incorporated and release a pyrophosphate (PPi) if it is complementary to the base in the target position, any release of the PPi being detected enzymatically, different deoxynucleotides or dideoxynucleotides being added either to separate aliqouuts of sample-primer mixture or successively to an aliquot of the same sample-primer mixture and subjected to the polymerase reaction to indicate which deoxynucleotide or dideoxynucleotide is incorporated, characterized in that, a PPi-detecting enzyme is included during the polymerase reaction step, and that deoxyadenosine triphosphate (dATP) or a dATP analog is used capable of acting as a substrate for polymerase but not capable of acting as a substrate for said PPi-detecting enzyme, instead of dATP or dideoxyadenosine triphosphate (ddATP). In JP-T No. 2001-506864, there is disclosed a method which advantageously permits a large scale unelectrophoretic solid phase DNA sequencing, thereby making successive determination of time-dependent progress of a polymerization reaction possible.

However, also in this method, a large scale equipment is required because detection by luminescence with luciferase and the like is required, which was not suitable as a simplified system for use in bed side at a hospital or use in drug supply.

In JP-A No. 63-49100, a method of measuring an inorganic phosphoric acid is disclosed. According to this method, a reaction including three steps involving an inorganic phosphoric acid is utilized, and finally, oxidized nicotinamide adenine dinucleotide ($NAD^+$) is reduced to give NADH, or oxidized nicotinamide adenine dinucleotide phosphate ($NADP^+$) is reduced to give NADPH. Amount of thus resulting NAD(P)H is measured by ultraviolet absorption method or the like. Because a reaction including three steps is used in this method, many elementary steps of the reaction are involved. Therefore, it is complicated to establish the reaction condition for allowing the entire elementary steps proceed. Further, it is not necessarily possible to predetermine an efficient condition. Moreover, it is required that comparatively large-scale equipment for the measurement such as spectrophotometer is used. Thus, there also existed problems involving lack of simpleness.

Moreover, similarly to the method described in the above JP-A No. 63-49100, a method of detecting a targeted sample is described in International Patent Publication pamphlet WO 00/04378 utilizing the reduction of a coenzyme NAD $(P)^+$ concurrent with a reaction of the targeted sample. However, since the targeted sample for detection therein is L-phenylalanine, such a method is not applicable to the detection of presence of a target nucleic acid molecule.

BRIEF SUMMARY OF THE INVENTION

An object of the present invention to solve the conventional problems as described hereinabove. Thus, the present invention provides a method of detecting an inorganic phosphoric acid, a pyrophosphate and a nucleic acid by a rapid and simple process, which enables detection with high sensitivity. Also, the present invention provides a SNP typing method which can put large quantity of SNP typing into practice with high sensitivity and at a low cost.

The present invention provides a method of detecting an inorganic phosphoric acid, which method comprises: subjecting a sample to a measurement system including glyceraldehyde-3-phosphate, oxidized nicotinamide adenine dinucleotide or oxidized nicotinamide adenine dinucleotide phosphate, glyceraldehyde phosphate dehydrogenase, and an electron mediator; and measuring a current value in the measurement system, wherein the current value indicates the concentration of the inorganic phosphoric acid in the sample.

In one embodiment, the electron mediator is at least one selected from the group consisting of a ferricyanide, 1,2-naphthoquinone-4-sulfonate, 2,6-dichlorophenol indophenol, dimethylbenzoquinone, 1-methoxy-5-methylphenazinium sulfate, methylene blue, gallocyanine, thionine, phenazine methosulfate, and Meldola Blue.

In one embodiment, the measurement system further includes diaphorase.

In one embodiment, the measurement system further includes adenosine diphosphate and phosphoglycerate kinase.

Further, the present invention provides a method of detecting a pyrophosphate, which method comprises: converting the pyrophosphate in a sample into an inorganic phosphoric acid; subjecting the sample to a measurement system including glyceraldehyde-3-phosphate, oxidized nicotinamide adenine dinucleotide or oxidized nicotinamide adenine dinucleotide phosphate, glyceraldehyde phosphate dehydrogenase, and an electron mediator; and measuring a current value in the measurement system, wherein the current value indicates the concentration of pyrophosphate in the sample.

In one embodiment, the aforementioned conversion of the pyrophosphate into an inorganic phosphoric acid is conducted using pyrophosphatase.

Moreover, the present invention provides a method of detecting a nucleic acid, which method comprises: subjecting a sample to a reaction system including a DNA probe having a complementary sequence to the sequence of the above nucleic acid, DNA polymerase and a deoxynucleotide, and allowing extension of the above DNA probe whereby a pyrophosphate produced concurrent with the extension reaction of the above DNA probe; converting the pyrophosphate produced in the sample into an inorganic phosphoric acid; subjecting the sample to a measurement system including glyceraldehyde-3-phosphate, oxidized nicotinamide adenine dinucleotide or oxidized nicotinamide adenine dinucleotide phosphate, glyceraldehyde phosphate dehydrogenase, and an electron mediator; and measuring a current value in the measurement system, wherein the current value indicates the concentration of the nucleic acid having a specified sequence in the sample.

In one embodiment, the extension reaction of the aforementioned DNA probe is a PCR reaction.

Furthermore, the present invention provides a method of typing a SNP sequence of a DNA, which method comprises: subjecting a sample to a reaction system including a DNA probe having a complementary sequence to the sequence of the above DNA and having a SNP site, DNA polymerase and a deoxynucleotide, and allowing extension of the above DNA probe whereby a pyrophosphate produced concurrent with the extension reaction of the above DNA probe; converting the pyrophosphate produced in the sample into an inorganic phosphoric acid; subjecting the sample to a measurement system including glyceraldehyde-3-phosphate, oxidized nicotinamide adenine dinucleotide or oxidized nicotinamide adenine dinucleotide phosphate, glyceraldehyde phosphate dehydrogenase, and an electron mediator; and measuring a current value in the measurement system, wherein the current value indicates the presence of the DNA having a specified sequence in the sample.

In one embodiment, the extension reaction of the aforementioned DNA probe is a PCR reaction.

These objects as well as other objects, features and advantages of the invention will become apparent to those skilled in the art from the following description with reference to the accompanying drawings.

DETAILED DESCRIPTION OF THE DRAWINGS

Figure 1:
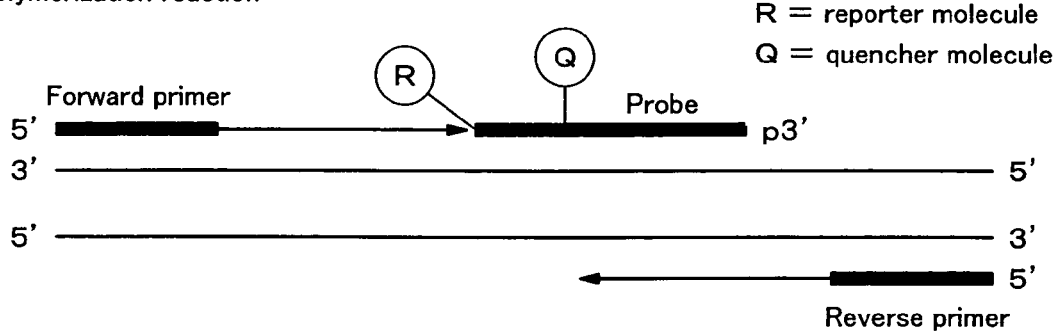
FIG. 1 is a diagrammic illustration showing a process of SNP typing by TaqMan PCR method.
Figure 1:
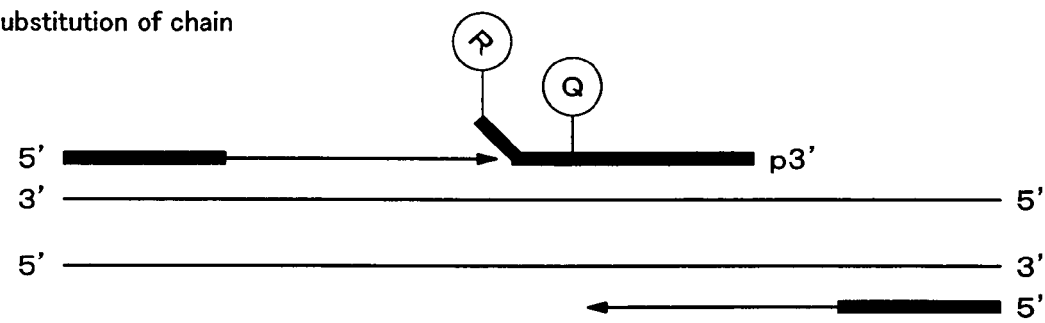
Figure 1:
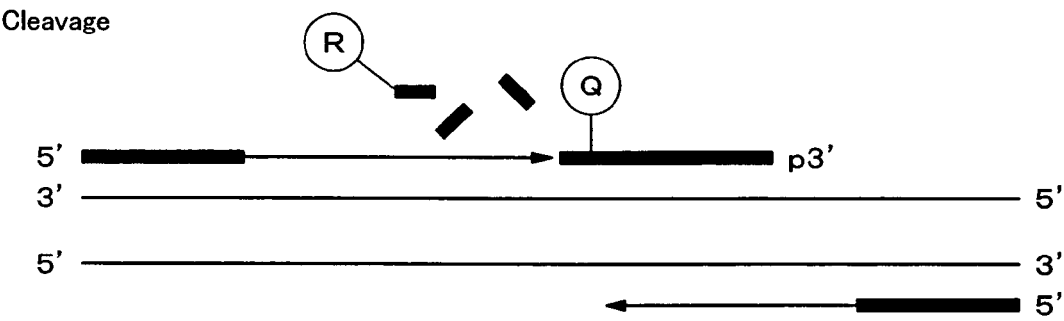
Figure 1:
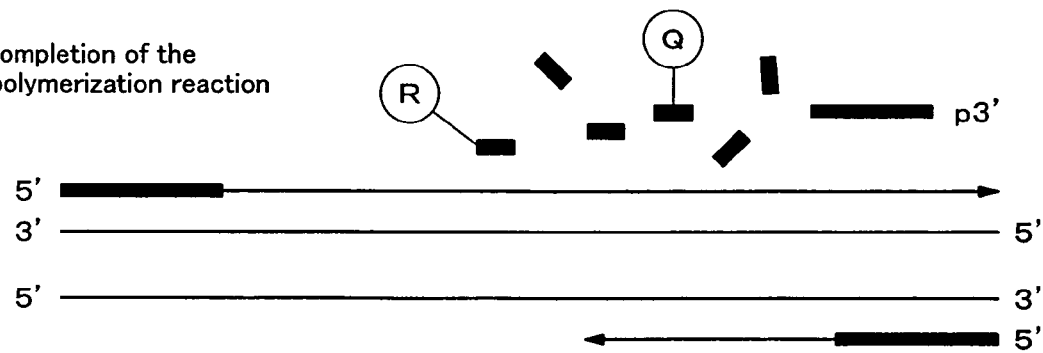
Figure 2:
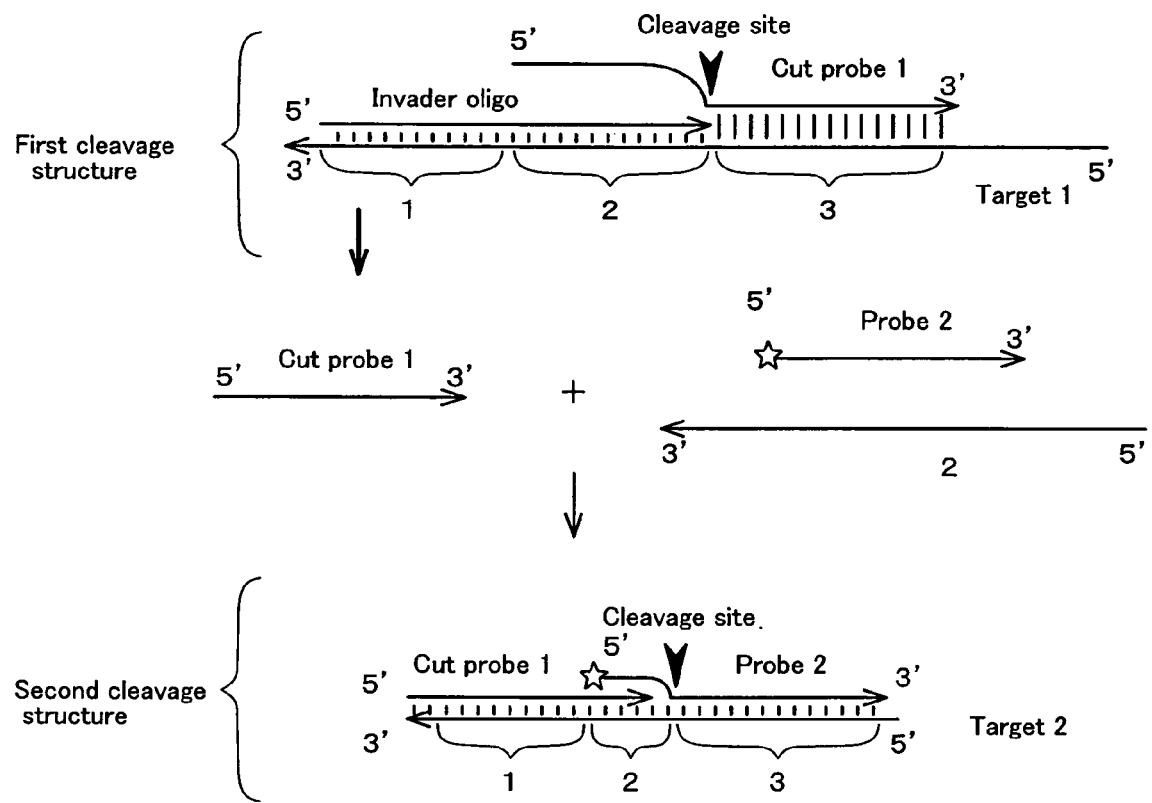
FIG. 2 is a diagrammic illustration showing a process of SNP typing by Invader method.
Figure 3:
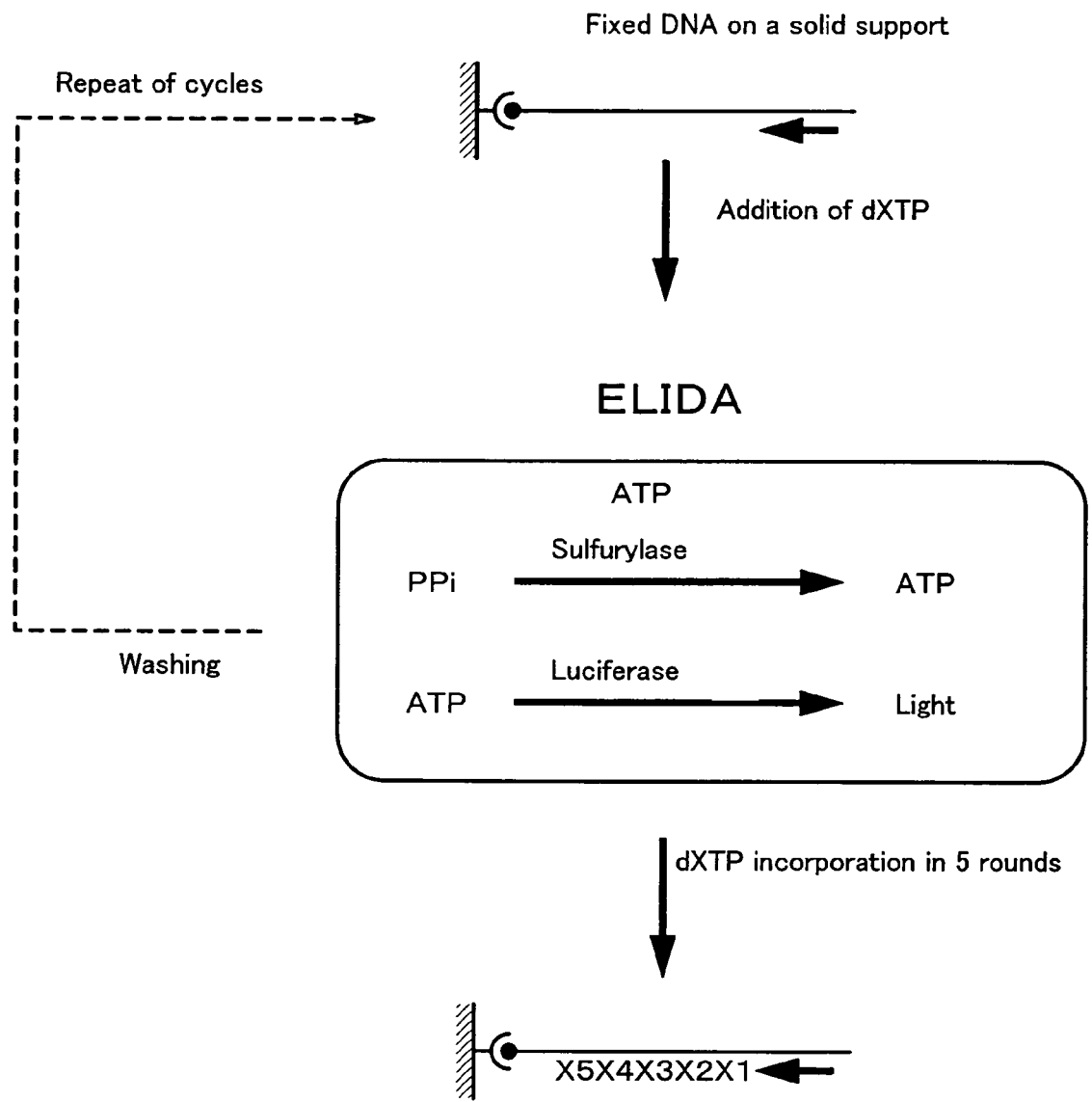
FIG. 3 is a diagrammic illustration showing a process of SNP typing by a pyrosequencing method.

Embodiments of the present invention are explained below.

EMBODIMENT 1

In accordance with the embodiment 1 of the present invention, quantitative detection of an inorganic phosphoric acid is carried out in a simple manner using an enzymatic reaction. The embodiment 1 of the present invention relates to a method of detecting an inorganic phosphoric acid, which method comprises: subjecting a sample to a measurement system including glyceraldehyde-3-phosphate, oxidized nicotinamide adenine dinucleotide ($NAD^+$) or oxidized nicotinamide adenine dinucleotide phosphate ($NADP^+$), glyceraldehyde phosphate dehydrogenase, and an electron mediator; and measuring a current value in this measurement system. The "measurement system" herein refers to a series of reactions as a whole involving in a mechanism relating to the detection of an inorganic phosphoric acid, and a field where such a series of reactions are executed. In the "measurement system", there exist components required for carrying out such a series of reactions. The "measurement system" can be usually provided in a solution form in which the aforementioned components are dissolved in an appropriate solvent (e.g., a buffer such as Tris-HCl buffer). Glyceraldehyde phosphate dehydrogenase refers to an enzyme that oxidatively phosphorylates glyceraldehyde-3-phosphate with $NAD^+$ or $NADP^+$ as a coenzyme. This enzyme may be also referred to herein as glyceraldehyde-3-phosphate dehydrogenase.

The embodiment 1 of the present invention is explained with reference to the reaction formula (I) through reaction formula (IV).

First, as represented by the reaction formula (I), an inorganic phosphoric acid is subjected to a catalytic action of glyceraldehyde-3-phosphate dehydrogenase and NAD(P)$^+$ together with glyceraldehyde-3-phosphate thereby converted into 1,3-bisphosphoglycerate. At the same time, NAD(P)$^+$ is reduced to give NAD(P)H.

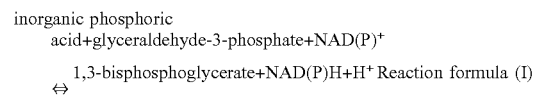

Next, by way of electron transfer from NAD(P)H produced in the reaction represented by the reaction formula (I), as represented by the reaction formula (II), an oxidized form of the electron mediator (Med(Ox) in the reaction formula (II)) is reduced to give a reduced form (Med(Re) in the reaction formula (II)). At the same time, NAD(P)H is oxidized to give NAD(P)$^+$.

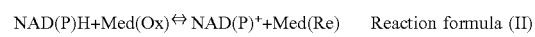

This reaction proceeds spontaneously when an appropriate electron mediator is used. The appropriate electron mediator may be such an electron mediator that the oxidized form thereof causes an oxidation reduction reaction with NAD(P)H, and the reduced form thereby produced is electrochemically oxidized at a working electrode to which electric potential of a certain level or greater is applied. Examples of the electron mediator which may be used in this embodiment include potassium ferricyanide, thionine, 1-methoxy-5-methylphenazinium methylsulfate, 2,6-dimethyl-P-benzoquinone, potassium 1,2-naphthoquinone-4-sulfonate, Meldola Blue, gallocyanine, methylene blue, indigo carmine, anthraquinone-1,5-disulfonate, safranine and the like. However, the electron mediator is not limited thereto as long as the oxidized form thereof causes an oxidation reduction reaction with NAD(P)H, and the reduced form thereby produced is electrochemically oxidized at a working electrode to which electric potential of a certain level or greater is applied. An enzyme which catalyzes the reaction represented by the reaction formula (II) can be also used for promoting the progress of the reaction. Examples of such an enzyme include diaphorase.

Finally, as represented by the reaction formula (III), the reduced form of the electron mediator which was produced as a result of the reaction represented by the reaction formula (II) is electrochemically oxidized at a working electrode to which electric potential of a certain level or greater is applied.

$$Med(Re) \leftrightarrow Med(Ox) + e^-$$ Reaction formula (III)

This oxidation results in release of en electron, and such release of an electron can be indicated as a current value. Measurement of such a current value can be performed using a general electrochemical detector.

Figure 9:
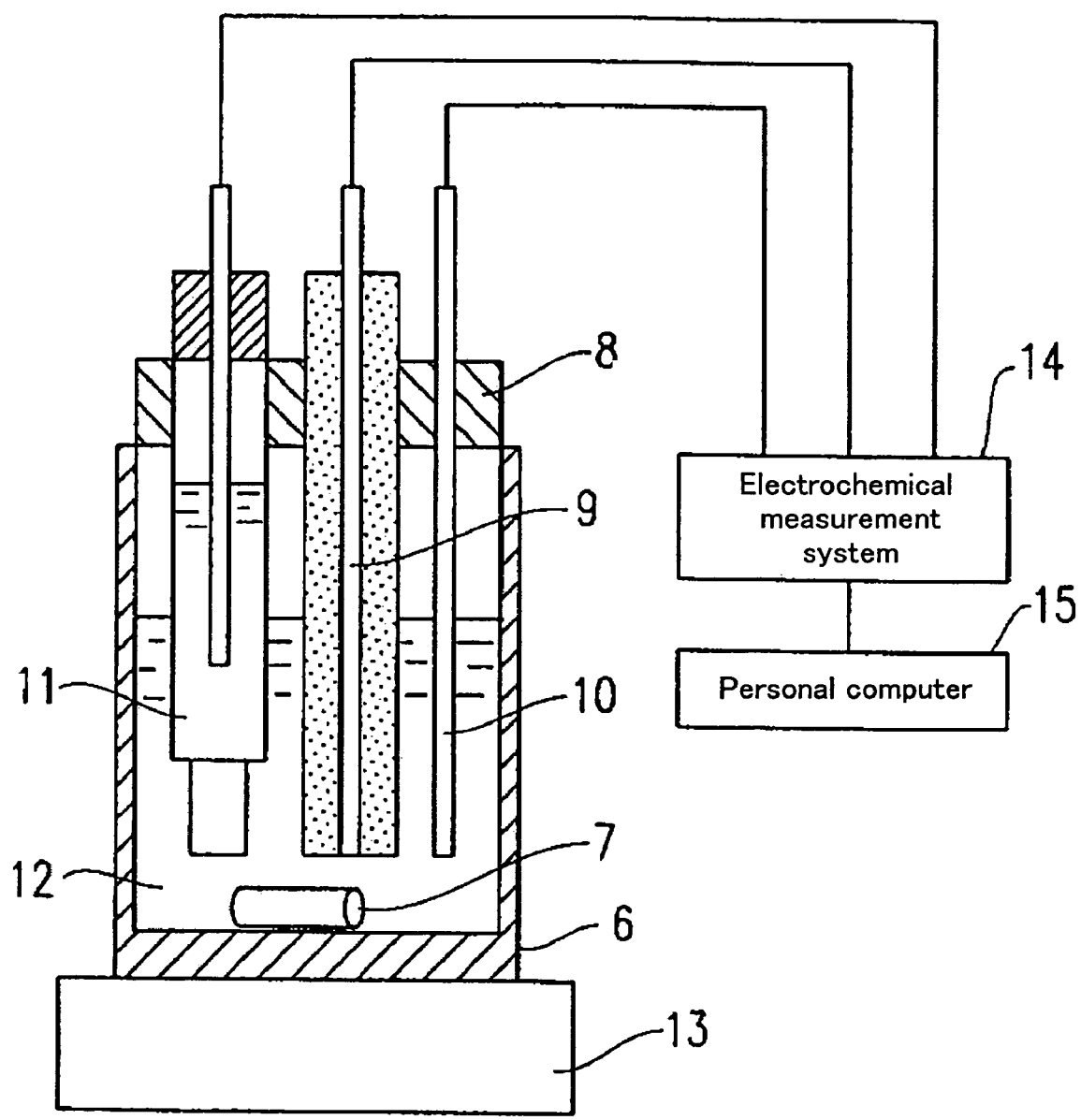
FIG. 9 is a schematic drawing illustrating an illustrative system of the measurement equipment for measuring the current value.

More specifically, the measurement of the electrochemical oxidation can be performed using a measurement equipment system shown in FIG. 9. This measurement equipment system is configured as follows. In the figure, 6 denotes a glass cell having a stirrer 7 placed therein, which is fixed on a stirrer machine 13. The glass cell 6 is equipped with a measurement electrode 9, a counter electrode 10 and a reference electrode 11 with an electrode fixing device 8. The measurement electrode 9 is composed of a gold electrode, and the counter electrode 10 is composed of a platinum wire, respectively. The reference electrode 11 is composed of a silver/silver chloride electrode, with a silver wire having a coating of silver chloride and a saturated KCl solution being connected to the glass cell via porous glass. These electrodes are respectively connected to an electrochemical measurement system 14 having a potentiostat, a function generator and the like integrated thereinto to effect control and data recording by a personal computer 15.

A reaction solution 12 is filled in the aforementioned glass cell 6, and the reaction solution 12 is agitated by the stirrer 7. When the electric potential of a certain level or greater in comparison with the reference electrode 11 is applied to the measurement electrode 9 using the electrochemical measurement system 14, the mediator in the reaction solution is oxidized. Thus, release of an electron resulting from this oxidation causes the current between the measurement electrode 9 and the counter electrode 10. The aforementioned electric potential varies depending on the mediator type. Higher electric potential than the oxidation reduction potential of the mediator type may be applied to the measurement electrode 9. For example, when potassium ferricyanide is used as a mediator, the electric potential of approximately +500 mV in comparison with the reference electrode 11 is applied to the measurement electrode 9. The current value hereby can be measured using the electrochemical measurement system 14.

Because the current value depends upon the presence of initially existing inorganic phosphoric acid, the inorganic phosphoric acid can be detected on the basis of this oxidation current value.

In the reaction formula (II), NAD(P)H is consumed through the reduction of the electron mediator leading to the production of NAD(P)$^+$. Therefore, the reaction represented by the reaction formula (I) is promoted in a direction to produce 1,3-bisphosphoglycerate and NAD(P)H. In other words, in accordance with this embodiment, the electron mediator is not only responsible for the measurement of the current value corresponding to the concentration of an inorganic phosphoric acid through being oxidized but also is responsible for the detection of the concentration of an inorganic phosphoric acid with high sensitivity.

In addition, as described above, en elementary process in which the inorganic phosphoric acid is involved is limited only to one step represented by the reaction formula (I) in this embodiment. Accordingly, it is easy to control the elementary process to allow for efficient progress.

The method of detection using a series of reactions represented by the reaction formula (I) to reaction formula (III) as demonstrated above enables qualitative detection of an inorganic phosphoric acid by an electrochemical process. Furthermore, because thus resulting current value depends on the amount of the initially existing inorganic phosphoric acid, such detection shall be quantitative.

In accordance with this embodiment, as represented by the reaction formula (I), an inorganic phosphoric acid, glyceraldehyde-3-phosphate and NAD(P)$^+$ react first, and consequently, 1,3-bisphosphoglycerate and NAD(P)H are produced. This reaction is an endergonic reaction. To the contrary, as represented by the reaction formula (IV), there exists a reaction in which 1,3-bisphosphoglycerate is subjected to a reaction by a catalytic action of phosphoglycerate kinase together with adenosine diphosphate (ADP) to produce 3-phosphoglycerate and adenosine triphosphate (ATP). In order to allow for progress of this reaction, Mg$^{2+}$ may also be added. Mg$^{2+}$ may be added in any form as long as it can be present in a state which permits participation to the reaction in the reaction system. Magnesium chloride may be preferably used. The concentration to be added may be 10 mM when each reaction substrate is added in an amount of 1 mM. This reaction is an exergonic reaction. Therefore, by conjugating the reaction represented by this reaction formula (IV) in this embodiment, equilibrium of the reaction represented by the reaction formula (I) may be shifted so that 1,3-bisphosphoglycerate and NAD(P)H are produced in a larger amount.

$$\text{1,3-bisphosphoglycerate} + \text{ADP} \xrightarrow{Mg^{2+}} \text{3-phosphoglycerate} + \text{ATP} \quad \text{Reaction formula (IV)}$$

As described above, for achieving detection of an inorganic phosphoric acid in a subject sample in accordance with this embodiment requires that the measurement system includes glyceraldehyde-3-phosphate, oxidized nicotinamide adenine dinucleotide or oxidized nicotinamide adenine dinucleotide phosphate, glyceraldehyde-3-phosphate dehydrogenase, and an electron mediator. This measurement system may also include diaphorase, thereby allowing for promotion of the reaction represented by the reaction formula (II). Also, this measurement system may include adenosine diphosphate and phosphoglycerate kinase as needed. The adenosine diphosphate and phosphoglycerate kinase act as represented by the reaction formula (IV) in this measurement system, and may promote the detection of the inorganic phosphoric acid.

The measurement system may be a reaction solution including each of the aforementioned components with an appropriate concentration. As is clear from the reaction formula (I) to reaction formula (IV), when glyceraldehyde-3-phosphate, oxidized nicotinamide adenine dinucleotide or oxidized nicotinamide adenine dinucleotide phosphate, and an electron mediator, and adenosine diphosphate are included, the adenosine diphosphate may be included in the reaction solution such that final concentration thereof becomes substantially identical. Enzymes such as glyceraldehyde-3-phosphate dehydrogenase, diaphorase and phosphoglycerate kinase may be included at an appropriate concentration to allow for progress of the reaction. Such a concentration may be 0.5 to 1,000 unit/ml, preferably 1 to 100 unit/ml, and most preferably 5 to 50 unit/ml when each reactive substance is added at a final concentration of about 1 mM, for example. For the purpose of detecting an inorganic phosphoric acid quantitatively, the sample is added to the reaction solution described above to cause the reactions as represented by the reaction formula (I) to reaction formula (III) (and reaction formula (IV)). Thus, the current value generated by these reactions can be measured.

EMBODIMENT 2

In accordance with the embodiment 2 of the present invention, simple quantitative detection of a pyrophosphate is carried out using an enzymatic reaction.

The embodiment 2 of the present invention is explained with reference to the reaction formula (V).

First, as represented by the reaction formula (V), a pyrophosphate (PPi in the reaction formula (V)) is hydrolyzed to give an inorganic phosphoric acid (Pi in the reaction formula (V)).

$$PPi + H_2O \leftrightarrow 2Pi \qquad \text{Reaction formula (V)}$$

This hydrolysis reaction may be carried out by raising the reaction temperature to reach a high temperature, and may be carried out using pyrophosphatase which is an enzyme that catalyzes this reaction.

Next, the pyrophosphate can be quantitatively detected through detecting the inorganic phosphoric acid produced by the reaction represented by the reaction formula (V) in a similar manner to the embodiment 1.

In accordance with this embodiment, it is not necessary to perform the reaction represented by the reaction formula (V) separately from the reaction for detecting the inorganic phosphoric acid demonstrated in the embodiment 1. Therefore, in order to detect a pyrophosphate in a subject sample, pyrophosphatase may be further included in the measurement system for detecting an inorganic phosphoric acid as explained for the embodiment 1 described above. For example, in order to detect a pyrophosphate in a subject sample, a reaction solution can be used including pyrophosphatase at an appropriate concentration in addition to the aforementioned each component included in the measurement system for detecting an inorganic phosphoric acid. This pyrophosphatase may also be included at an appropriate concentration to allow for progress of the reaction. The concentration of this pyrophosphatase may be 0.001 to 1,000 unit/ml, preferably 0.01 to 100 unit/ml, and most preferably 0.1 to 1 unit/ml when each reactive substance is added at a final concentration of about 1 mM, for example. For the purpose of detecting the pyrophosphate quantitatively, the sample is added to the reaction solution described above to cause the reactions as represented by the reaction formula (V) and the reaction formula (I) through reaction formula (III) (and reaction formula (IV)). Thus, the current value generated by these reactions can be measured.

EMBODIMENT 3

In accordance with the embodiment 3 of the present invention, a method of detecting a DNA having a specified sequence with high sensitivity is carried out.

In this embodiment, a sample is first subjected to a reaction system including a DNA probe having a complementary sequence to the sequence of a targeted DNA, DNA polymerase and a deoxynucleotide. The "reaction system" herein refers to a series of nucleic acid extension reactions as explained below, and a field where such reactions are executed. In the "reaction system", there exist components required for carrying out such a series of reactions. The "reaction system" can be usually provided in a solution form in which the aforementioned components are dissolved in an appropriate solvent (e.g., Tris-HCl buffer, any buffer which may be generally used in a nucleic acid extension reaction or a nucleic acid amplification reaction (buffers included in commercially available kits may be involved)). The DNA polymerase may be optional DNA polymerase which is commercially available, or can be prepared by a person skilled in this art. Preferably, Taq polymerase may be used, but not limited thereto. The deoxynucleotide may be each deoxynucleoside triphosphate (also referred to as dNTP: including deoxycytosine triphosphate, deoxyguanine triphosphate, deoxyadenine triphosphate, and deoxythymidine triphosphate), which is a substance that is generally used as a precursor for DNA synthesis. Accordingly, extension of a DNA probe is allowed, thereby producing a pyrophosphate concurrent with this extension reaction of the DNA probe. This reaction is explained with reference to the reaction formula (VI).

When this DNA probe is hybridized to a targeted DNA, extension is executed by the DNA polymerase which is present in the reaction system through incorporating therein one deoxynucleotide (dNTP in the reaction formula (VI)) in the reaction system to produce one molecule of the pyrophosphate.

$$DNA_{(n)} + dNTP \leftrightarrow DNA_{(n+1)} + PPi \qquad \text{Reaction formula (VI)}$$

In the reaction formula (VI), the subscripts n and n+1 represent number of bases of the DNA probe. Therefore, the reaction formula (VI) represents that the DNA probe having n bases were extended to have n+1 bases by this reaction. Thus produced pyrophosphate is degraded into an inorganic phosphoric acid similarly to the embodiment 2 followed by detection of the inorganic phosphoric acid similarly to the embodiment 1. Accordingly, detection of a DNA having a specified sequence in a sample is enabled.

The DNA probe used in this embodiment is designed such that it has a complementary sequence to the sequence of the targeted DNA for detection. When this DNA probe is hybridized to the sequence of the targeted DNA for detection, it serves as a primer for extension of the DNA probe. Therefore, the length of the DNA probe is long enough to serve as a primer for the extension reaction. For example it may be at least 10 bases, at least 12 bases, at least 15 bases, at least 20 bases, at least 30 bases, at least 40 bases, and at least 50 bases in length. Taking into account of capability of conducting sufficient hybridization and primer extension, and feasibility of the preparation thereof, it is preferably 15 to 50 bases in length. The DNA probe used in the method of the present invention may have any length as long as it specifically hybridizes to the targeted DNA for detection, and serves as a primer for extension of the DNA probe.

For specific hybridization of the DNA probe to the targeted DNA in a sample and for serving as a primer, when the sequence to be detected is known, the DNA probe may be designed so that it has a sequence which is completely complementary to this sequence, i.e., a sequence that accurately corresponds to bases in the sequence (A-T or C-G pair). When there exists no DNA having the targeted specified sequence in a sample, hybridization to the DNA probe does not occur, as a matter of course. Therefore, by using this reaction system, presence of a sequence which is completely complementary to this DNA probe can be detected regardless of whether or not the sequence to be detected is known.

Although the hybridization and extension reaction may be preferably carried out under an essentially similar condition to that in the following Example 4, it may be performed under an arbitrary condition in which hybridization of a DNA, and the extension reaction of a DNA to a primer and a deoxynucleotide by an action of DNA polymerase are performed. Hybridization of a DNA probe to a targeted DNA may be performed by a method which is described in a text for experiments such as for example, Sambrook et al., (1989) Molecular Cloning: A Laboratory Manual, Second Edition, Vol. 1 to 3, Cold Spring Harbor Laboratory or the like, and such a method is known to persons skilled in this art. Typically, the hybridization condition for the temperature may be usually predetermined by calculating Tm value through adding 2° C. to a sum obtained on the basis of A-T pairs (2° C. per A-T pair) and G-C pairs (4° C. per G-C pair) followed by subtracting approximately 5° C. from the Tm value. In accordance with the embodiment of present invention, because high specificity is desired, the hybridization maybe conducted at 50 to 60° C. for about 1 second. Conditions of the extension reaction by the polymerase may be predetermined in light of conditions in which this enzyme suitable reacts. When Taq polymerase is employed, the reaction may be performed at 70 to 74° C. Time period for the reaction may be approximately from 10 seconds to 3 minutes.

Amount of the DNA probe, polymerase and deoxynucleotide which may be included in the reaction system may be determined ad libitum by a person skilled in this art.

In addition, as represented by the reaction formula (VI), each extension with one deoxynucleotide produces each one pyrophosphate. Therefore, when both lengths (bases) of the DNA having the targeted specified sequence and the DNA probe are known, quantitative detection of the DNA having the targeted specified sequence is possible.

Moreover, by substituting the reaction represented by the reaction formula (VI) for the reaction of a nucleic acid amplification reaction such as PCR or the like, the amount of the DNA having the targeted specified sequence in a sample can be increased dramatically. Method for the PCR amplification is known in this art (PCR Technology: Principles and Applications for DNA Amplification, H A Erlich Ed., Freeman Press, New York, N.Y. (1992); PCR Protocols: A Guide to Methods and Applications, Innis, Gelfland, Snisky, and White Ed., Academic Press, San Diego, Calif. (1990); Mattila et al., (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford). By using a nucleic acid amplification reaction such as PCR or the like, detection of a trace amount of a DNA is also enabled.

Although a method of detecting a DNA having a specified sequence with high sensitivity was demonstrated in this embodiment, it is possible to detect also an RNA having a specified sequence by a similar method.

EMBODIMENT 4

In accordance with the embodiment 4 of the present invention, a method of rapidly typing a SNP of a DNA in a measurement system is performed.

Figure 4:
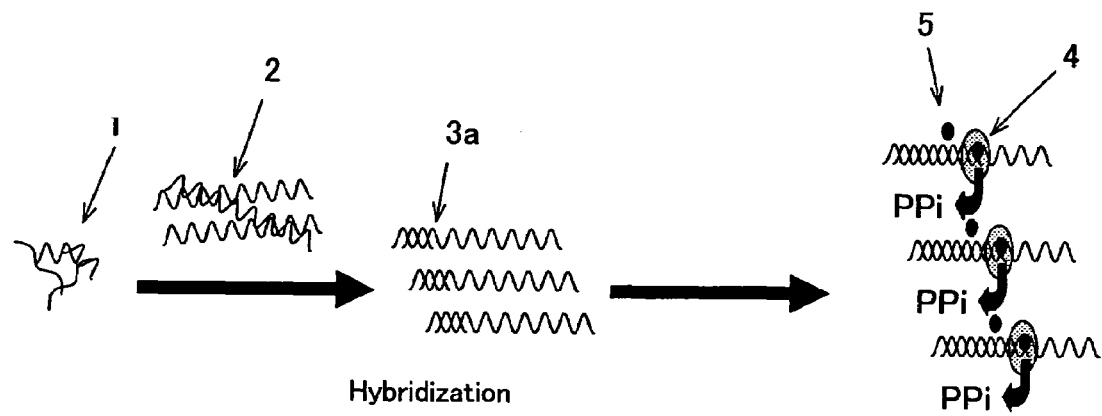
FIG. 4 is a schematic drawing illustrating production of pyrophosphate through the use of a SNP site matched probe.
Figure 5:
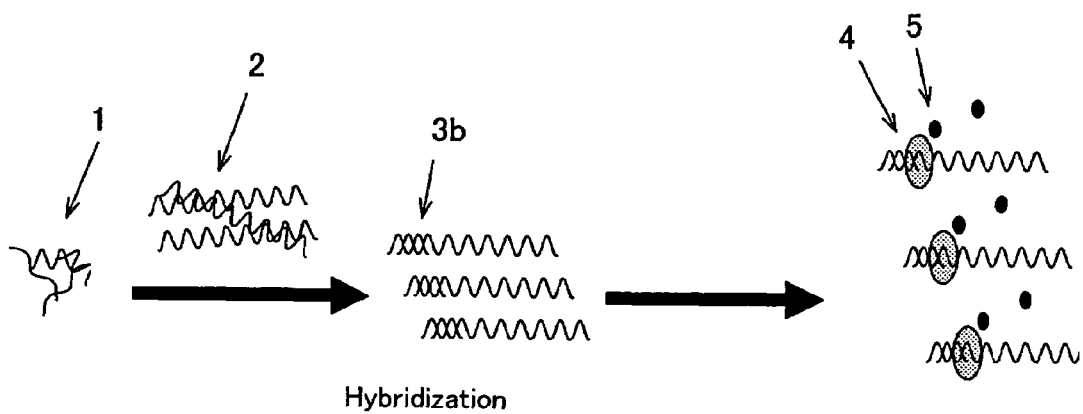
FIG. 5 is a schematic drawing illustrating an aspect through the use of a SNP site mismatched probe.

The embodiment 4 of the present invention is explained with reference to FIG. 4 and FIG. 5. FIG. 4 shows a reaction system in which SNP sites are matched between a targeted DNA for detection and a DNA probe. FIG. 5 shows a reaction system in which SNP sites are mismatched between a targeted DNA for detection and a DNA probe. In FIG. 4 and FIG. 5, 1 denotes a DNA probe, 2 denotes a DNA having a targeted specified sequence, 3a denotes a matched SNP site, 3b denotes a mismatched SNP site, 4 denotes DNA polymerase, and 5 denotes dNTP.

In this embodiment, a sample is first subjected to a reaction system including a DNA probe having a complementary sequence to the sequence of a targeted DNA and the 3' end thereof being a SNP site, DNA polymerase and a deoxynucleotide. Accordingly, the DNA probe is extended where a pyrophosphate is produced concurrent with this extension reaction of the DNA probe.

The DNA probe used in this embodiment is designed so that it is complementary to the targeted sequence, and the 3' end thereof being a SNP site. In this embodiment, the DNA probe may be similarly designed to the above embodiment 3 except that the 3' end is a SNP site. The DNA polymerase and the deoxynucleotide used in this embodiment may be similar to those which may be used in the above embodiment 3. Conditions for the hybridization and extension employed in this embodiment may be also similar to those which may be employed in the above embodiment 3.

When base sequences of the targeted DNA in the sample and the DNA probe are completely complementary including the SNP site, the DNA probe hybridizes to the targeted DNA, and serves as a primer for additional extension of the probe. In this instance, as shown in FIG. 4, extension of the DNA probe is executed with one deoxynucleotide by DNA polymerase which is present in the reaction system to produce one molecule of the pyrophosphate. To the contrary, when base sequences of the targeted DNA in the sample and the DNA probe are not complementary in the SNP site, even though complementarity is found in other part, the DNA probe does not serve as a primer for the extension of the probe because the 3' end of the DNA probe is mismatched, although hybridization to the targeted DNA can be carried out. In this instance, as shown in FIG. 5, the reaction represented by the reaction formula (VI) does not occur even though DNA polymerase and a required deoxynucleotide are present in the reaction system, and thus a pyrophosphate is not produced.

Accordingly, the DNA having the targeted specified sequence in the sample and the DNA probe can be discriminated as completely matched including the SNP site, through degradation of the pyrophosphate in the sample following the extension reaction of the nucleic acid into an inorganic phosphoric acid in a similar manner to the embodiment 2, and then detecting the inorganic phosphoric acid similarly to the embodiment 1. When at most 4 kinds of probes are used having different kinds of bases in their SNP sites, it is possible to perform typing of a SNP of a DNA having a specified sequence in a sample for the 4 kinds of bases.

Additionally, when the kind of the base in the SNP site is known, such 4 kinds of probes are not necessarily required for typing, as a matter of course.

In this embodiment, a DNA probe with the 3' end being a SNP site was used, however, typing of a SNP of a DNA can be also performed even though a DNA probe having a SNP site at any base other than the 3' end is used.

The term "sample" which may be used in the present invention refers to any sample which can finally include an inorganic phosphoric acid. In the embodiment 2, the sample may include a pyrophosphate which is converted into an inorganic phosphoric acid; and in the embodiments 3 and 4, the sample may include a DNA for the production of a pyrophosphate to be converted into an inorganic phosphoric acid by an extension reaction. In particular, in the method of detecting a DNA (Embodiment 3 or 4), the "sample" may be derived from an arbitrary subject analyte which may contain a targeted DNA. Such a subject analyte maybe any one of suffered cells, tissues, organs or blood from a disease when the targeted DNA may relate to the disease. As a matter of course, the method of the present invention is not limited to clinical applications, but can be used in all fields. Thus, such subject analyte may be any one of cells, tissues, organs or blood in which the targeted DNA is expressed or the presence thereof has been proven. The DNA can be extracted from such a subject analyte using a conventional process such as a phenol extraction process or alcohol precipitation. Purity of a DNA may exert an influence on the efficiency of the reaction, and procedures for the purification of a DNA are also known to persons skilled in this art.

As is explained hereinabove, quantitative detection of an inorganic phosphoric acid in a sample with high sensitivity using an electrochemical process is enabled by including glyceraldehyde-3-phosphate, oxidized nicotinamide adenine dinucleotide or oxidized nicotinamide adenine dinucleotide phosphate, glyceraldehyde-3-phosphate dehydrogenase and an electron mediator, and diaphorase as needed in a measurement system, according to the present invention. Furthermore, by including adenosine diphosphate and phosphoglycerate kinase in the aforementioned measurement system, more rapid measurement is enabled.

In addition, degradation of a pyrophosphate into an inorganic phosphoric acid using pyrophosphatase allows for quantitative measurement with high sensitivity and at a high speed using the method as described above.

Moreover, according to the present invention, presence of a targeted nucleic acid can be quantitatively determined by measuring a pyrophosphate produced concurrent with the extension reaction of a nucleic acid. Furthermore, determination of a base in a SNP site of a targeted nucleic acid can be performed with high sensitivity and at a high speed.

Hence, according to the present invention, typing of a SNP of a targeted nucleic acid in a simple and rapid manner is enabled without labeling the targeted nucleic acid in a sample.

EXAMPLES

Detection of an inorganic phosphoric acid, detection of a pyrophosphate, detection of a DNA, and typing of a SNP according to the present invention are more specifically explained below. The present invention is not limited to the following examples. Materials, reagents and the like used in the Examples are available from any commercial source unless otherwise specified.

Example 1

Figure 6:
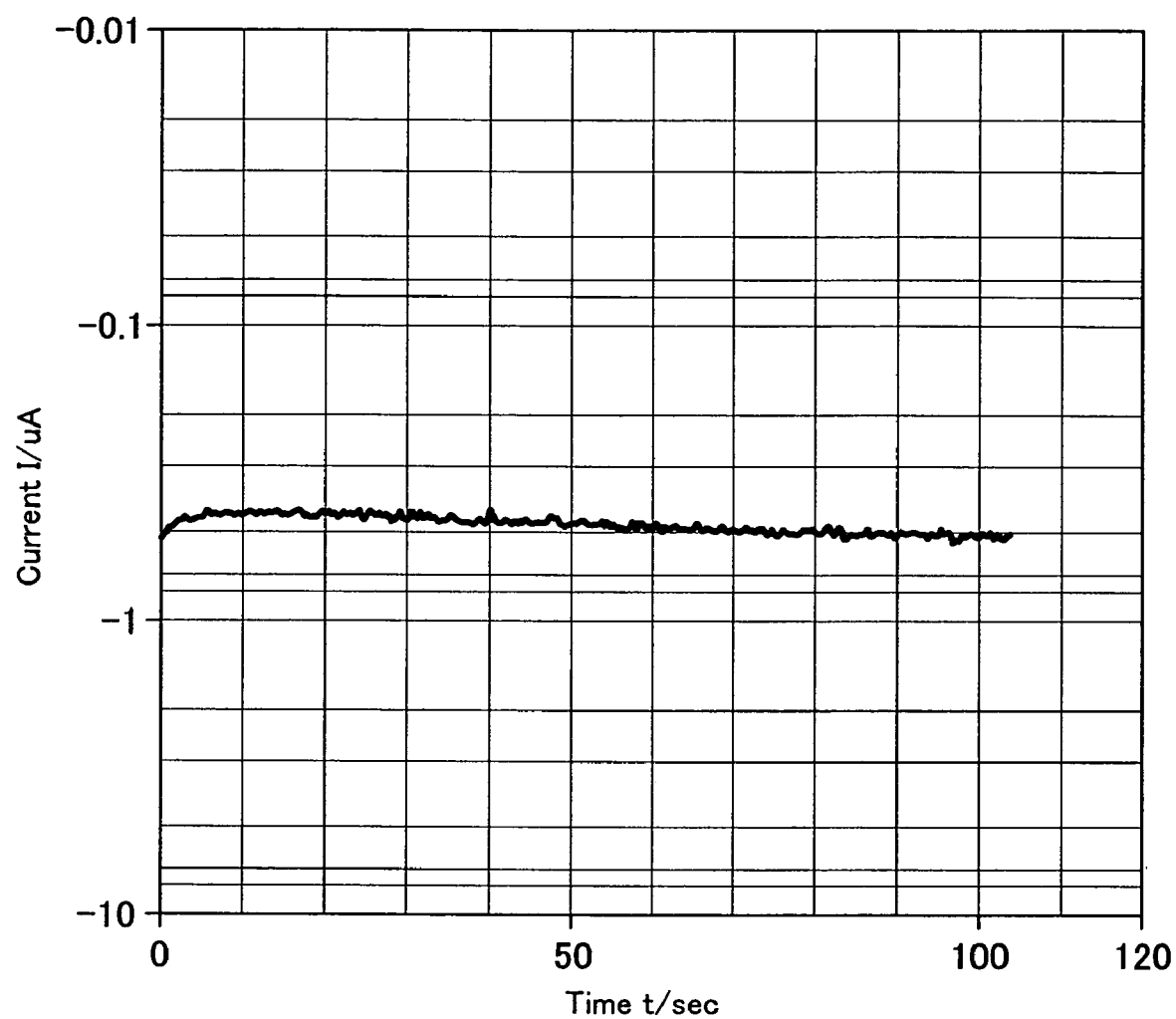
FIG. 6 is a graph showing the reaction time of detection of phosphoric acid in Example 1.
Figure 7:
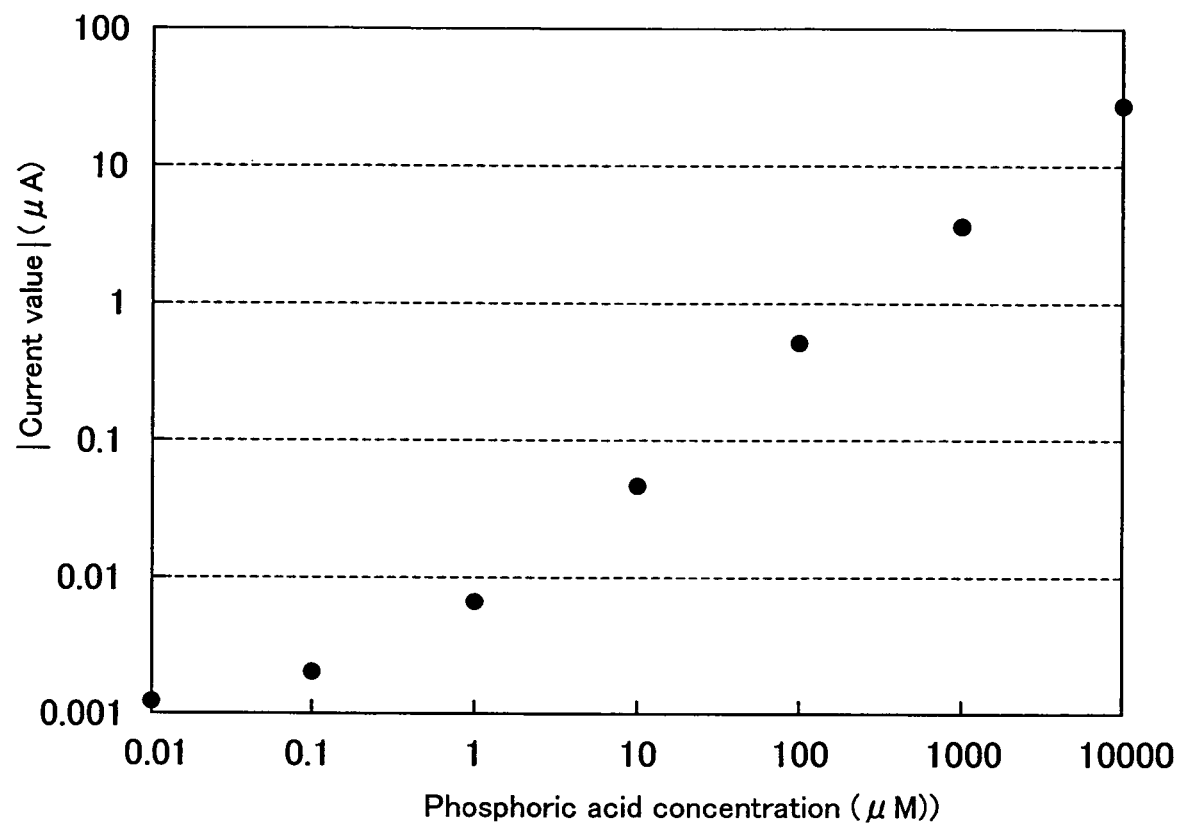
FIG. 7 is a graph showing a relationship between the concentration of phosphoric acid and the current value in Example 1.

A reaction solution was prepared by the following procedure. In 100 mM Tris-HCl buffer were dissolved 1.8 µl of 282 mM glyceraldehyde-3-phosphate (final concentration: 1 mM), 10 µl of 50 mM oxidized nicotinamide adenine dinucleotide (final concentration: 1 mM), 10 µl of 1 unit/µl glyceraldehyde-3-phosphate dehydrogenase (final concentration: 20 unit/ml), 10 µl of 1 unit/µl diaphorase (final concentration: 20 unit/ml) and 10 µl of 50 mM potassium ferricyanide (final concentration: 1 mM). The mixture was adjusted to the pH of 7.5 and the total volume of 500 µl. To this reaction solution was added 1 µl of 50 mM phosphoric acid (final concentration: 0.1 mM). This reaction solution was subjected to a measurement equipment system configured as shown in FIG. 9. This measurement equipment system has the following configuration. A glass cell 6 having a stirrer 7 placed therein was fixed on a stirrer machine 13. The glass cell 6 was equipped with a measurement electrode 9, a counter electrode 10 and a reference electrode 11 with an electrode fixing device 8. The measurement electrode 9 was composed of a gold electrode, and the counter electrode 10 was composed of a platinum wire, respectively. The reference electrode 11 was composed of a silver/silver chloride electrode, with a silver wire having a coating of silver chloride and a saturated KCl solution being connected to the glass cell via porous glass. These electrodes were respectively connected to an electrochemical measurement system (manufactured by Hokuto Denko Corporation, in the figure, denoted by 14) to effect control and data recording by a personal computer 15. The aforementioned reaction solution was filled in the glass cell 6 described above. This reaction solution was agitated by the stirrer 7. Using the electrochemical measurement system, the electric potential of +500 mV in comparison with the reference electrode 11 was applied to the measurement electrode 9. The mediator in the reaction solution was thereby oxidized, and thus, release of an electron resulting from this oxidation caused the current between the measurement electrode 9 and the counter electrode 10. The caused current value was measured using the electrochemical measurement system. Alteration of the current value is illustrated in FIG. 6. In FIG. 6, the current I (µA) is indicated by the longitudinal axis, and time t (sec) is indicated by the horizontal axis. From FIG. 6, it was revealed that this reaction reached to a steady level in about 100 seconds. Next, the current value after 100 seconds passed is illustrated in FIG. 7 when the amount of the phosphoric acid was varied. In FIG. 7, the absolute value of the current value (µA) is indicated by the longitudinal axis; the concentration of phosphoric acid (µM) is indicated by the horizontal axis; and the current value at each phosphoric acid concentration is depicted by a black circle. As shown in FIG. 7, the current value after 100 seconds passed exhibited a favorable linear relationship with the amount of the phosphoric acid as added.

Example 2

A reaction solution was prepared by the following procedure. In 100 mM Tris-HCl buffer were dissolved 1.8 µl of 282 mM glyceraldehyde-3-phosphate (final concentration: 1 mM), 10 µl of 50 mM oxidized nicotinamide adenine dinucleotide (final concentration: 1 mM), 10 µl of 1 unit/µl glyceraldehyde-3-phosphate dehydrogenase (final concentration: 20 unit/ml), 10 µl of 50 mM adenine diphosphate (final concentration: 1 mM) and 10 µl of 1 unit/µl phosphoglycerate kinase (final concentration: 20 unit/ml), 10 µl of 1 unit/µl diaphorase (final concentration: 20 unit/ml), 10 µl of 50 mM potassium ferricyanide (final concentration: 1 mM) and 10 µl of 50 mM magnesium chloride (final concentration: 10 mM). The mixture was adjusted to the pH of 7.5 and the total volume of 500 µl. To thus prepared reaction solution was added 1 µl of 50 mM phosphoric acid (final concentration: 0.1 mM), then the current value was measured similarly to Example 1. In this Example, the reaction reached to a steady level in about 60 seconds. Hence, it was ascertained that the reaction was promoted by adding adenosine diphosphate and phosphoglycerate kinase.

Example 3

Figure 8:
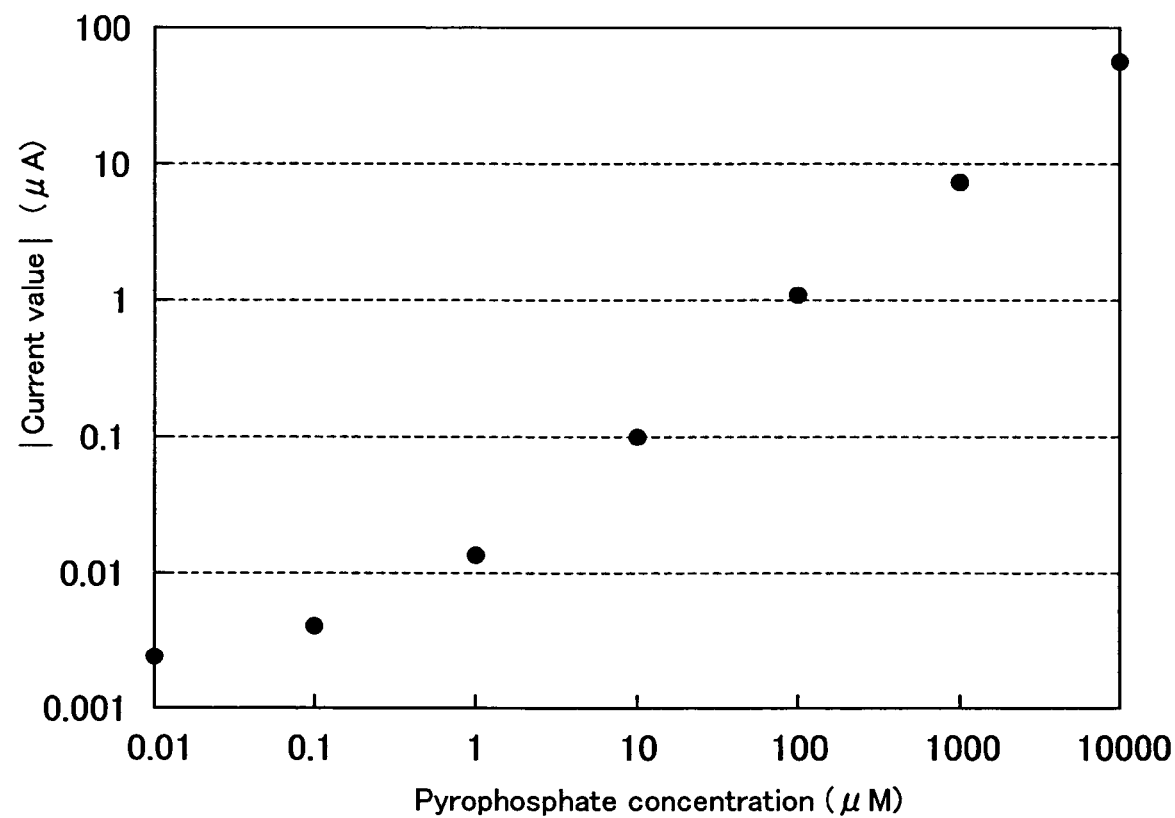
FIG. 8 is a graph showing a relationship between the concentration of pyrophosphate and the current value in Example 3.

A reaction solution was prepared by the following procedure. In 100 mM Tris-HCl buffer were dissolved 10 µl of 1 unit/µl pyrophosphatase (final concentration: 20 unit/ml), 1.8 µl of 282 mM glyceraldehyde-3-phosphate (final concentration: 1 mM), 10 µl of 50 mM oxidized nicotinamide adenine dinucleotide (final concentration: 1 mM), 10 µl of 1 unit/µl glyceraldehyde-3-phosphate dehydrogenase (final concentration: 20 unit/ml), 10 µl of 1 unit/µl diaphorase (final concentration: 20 unit/ml) and 10 µl of 50 mM potassium ferricyanide (final concentration: 1 mM). The mixture was adjusted to the pH of 7.5 and the total volume of 500 µl. To thus prepared reaction solution was added 1 µl of 50 mM pyrophosphate (final concentration: 0.1 mM), then the current value after 100 seconds passed was measured similarly to Example 1 (results not shown). The current value after 100 seconds passed when the amount of pyrophosphate was varied is illustrated in FIG. 8. In FIG. 8, the absolute value of the current value (µA) is indicated by the longitudinal axis; the concentration of pyrophosphate (µM) is indicated by the horizontal axis; and the current value at each pyrophosphate concentration is depicted by a black circle. As shown in FIG. 8, the current value exhibited a favorable linear relationship for the concentration of the pyrophosphate as added.

Example 4

For a sample, which was referred to as sample 1, with Control Template (λDNA) (manufactured by TaKaRa Shuzo Co., Ltd.) added to its measurement system; or for a sample, which was referred to as sample 2, without the addition, a PCR reaction was carried out. Experiments were conducted using λDNA as a template, and as primers, Control Primer 1 (5'-GATGAGTTCGTGTCCGTACAACT-3' (SEQ ID NO: 1)) and Primer 3 (5'-GGTTATCGAAATCAGCCACAGCGCC-3' (SEQ ID NO: 2)) of TaKaRa PCR Amplification kit (manufactured by TaKaRa Shuzo Co., Ltd.) (for use in amplification of 500 bp). After adding 0.5 µl of 2.5 unit/µl TaKaRa Z-Taq™, 5 µl of 10×Z-Taq™ Buffer, 4 µl of 2.5 mM each dNTP Mixture, each 0.5 µl of 20 pmol/µl Primer 1 and Primer 3 to the sample 1 and the sample 2 respectively, 1 µl of 1 µg/ml λDNA was added only to the sample 1. Then distilled water was added to the sample 1 and the sample 2 respectively to give the total volume of 50 µl. The PCR reaction was carried out with 30 cycles of: 98° C. for 1 sec, 55° C. for 1 sec, and 72° C. for 10 sec. To the reaction solution prepared in Example 3 (prior to adding pyrophosphate) was added 1 µl of the solution in which the PCR reaction was completed, and the current value after 100 seconds passed was measured similarly to Example 1. Results are shown in Table 1.

TABLE 1

| | Sample 1 | Sample 2 |
|---|---|---|
| Current value | 552 nA | 21 nA |

As for the sample 1 with DNA added as a template, oxidation current of potassium ferricyanide was observed according to the progress of the enzymatic reaction beginning with pyrophosphate produced upon the progress of the PCR reaction. However, as for the sample 2, the PCR reaction did not proceed, and thus, the current was not observed.

Example 5

Control Template (λDNA) (supra) was added to a measurement system, and a PCR reaction was carried out. Experiments were conducted using λDNA as a template, and for a sample 1, Control Primer 1 (5'-GATGAGTTCGTGTCCGTACAACT-3' (SEQ ID NO: 1)) and Primer 3 (5'-GGTTATCGAAATCAGCCACAGCGCC-3' (SEQ ID NO: 2)); and for the sample 2, modified Primer 1' (5'-GATGAGTTCGTGTCCGTACAACA-3' (SEQ ID NO: 3)) and Primer 3 of TaKaRa PCR Amplification Kit (manufactured by TaKaRa Shuzo Co., Ltd.) (for use in amplification of 500 bp) were used as primers. After adding 0.5 µl of 2.5 unit/µl TaKaRa Z-Taq™, 5 µl of 10×Z-Taq™ Buffer, 4 µl of 2.5 mM each dNTP Mixture, and to the sample 1, each 0.5 µl of 20 pmol/µl Primer 1 and Primer 3; and to the sample 2, each 0.5 µl of 20 pmol/µl Primer 1' and Primer 3, respectively, thereto were added 1 µl of 1 µg/ml λDNA and distilled water, respectively, to give the total volume of 50 µl. The PCR reaction was carried out with 30 cycles of: 98° C. for 1 sec, 55° C. for 1 sec, and 72° C. for 10 sec. To the reaction solution prepared in Example 3 (prior to adding pyrophosphate) was added 1 µl of the solution in which the PCR reaction was completed, and the current value after 100 seconds passed was measured similarly to Example 1. Results are shown in Table 2.

TABLE 2

| | Sample 1 | Sample 2 |
|---|---|---|
| Current value | 468 nA | 83 nA |

As for the sample 1 in which Primer 1 and Primer 3 as primers were used which were completely complementary to the base sequence of λDNA which was a template, oxidation current of potassium ferricyanide was observed according to the progress of the enzymatic reaction beginning with pyrophosphate produced upon the progress of the PCR reaction. However, as for the sample 2, because the 3' terminal end of Primer 1' is not complementary to the base sequence of λDNA which was a template, only an extension reaction by Primer 3 was executed with the template λDNA as a template, without progress of the amplification reaction by PCR. Accordingly, scarcely any current was observed.

Example 6

A reaction solution was prepared by the following procedure. In 50 mM Tricine-NaOH buffer were dissolved 50 µl of 1 mM pyrophosphate (final concentration: 100 µM) 17.5

µl of 30 mM glyceraldehyde-3-phosphate (final concentration: 1 mM), 50 µl of 10 mM oxidized nicotinamide adenine dinucleotide (final concentration: 1 mM), 50 µl of 10 mM potassium ferricyanide (final concentration: 1 mM), 8.0 µl of 100 mM magnesium chloride (final concentration: 1.6 mM), 5 µl of 1 unit/µl diaphorase (final concentration: 10 unit/ml) and 1 µl of 0.2 unit/µl pyrophosphatase (final concentration: 0.4 unit/ml). The mixture was adjusted to the pH of 8.8 and the total volume of 480 µl.

Figure 10:
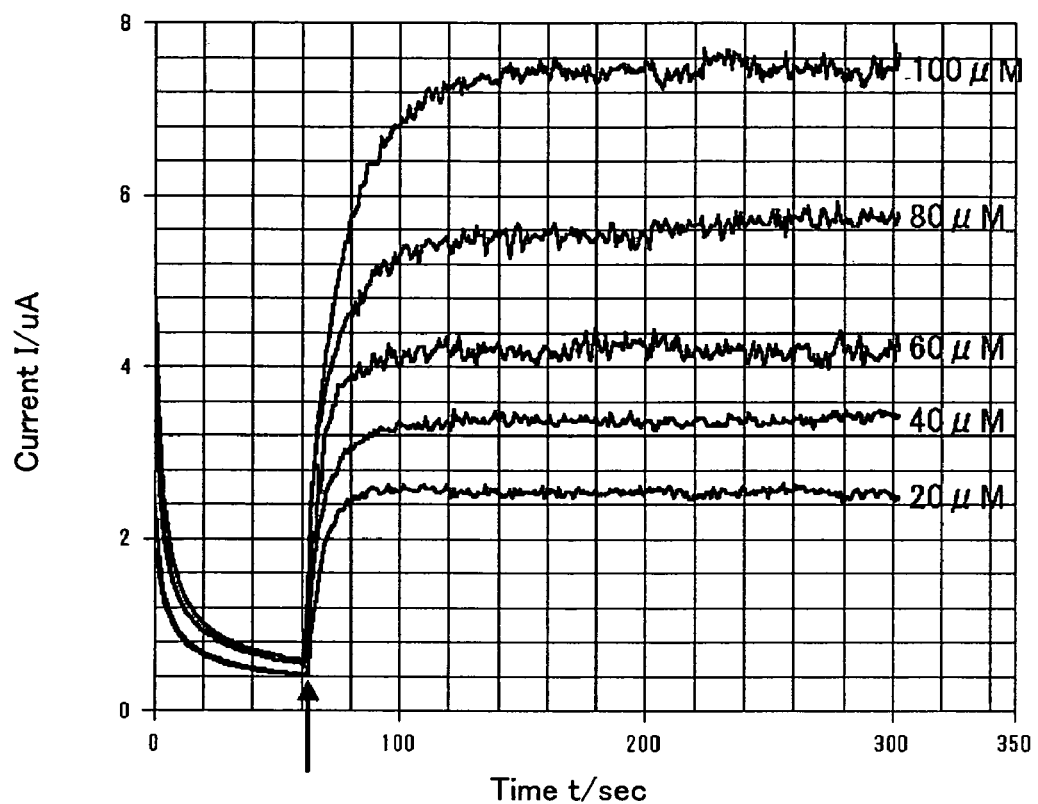
FIG. 10 is a graph showing the reaction time of detection of pyrophosphate in Example 6.

While measuring the current value similarly to Example 1, to thus prepared reaction solution was added 20 µl of 0.8 unit/µl glyceraldehyde-3-phosphate dehydrogenase (final concentration: 32 unit/ml) after 60 seconds passed since the measurement was started. Furthermore, the current value was similarly measured which was observed when the aforementioned pyrophosphate of 1 mM was changed to 0.8 mM (final concentration: 80 µM), 0.6 mM (final concentration: 60 µM), 0.4 mM (final concentration: 40 µM) and 0.2 mM (final concentration: 20 µM), respectively. Alteration of thus obtained current value is illustrated in FIG. 10. In FIG. 10, the current I (µA) is indicated by the longitudinal axis, and time t (sec) is indicated by the horizontal axis. From FIG. 10, it was revealed that this reaction reached to a steady level in about 100 seconds after initiating the reaction (about 160 seconds from the initiation of the measurement).

Figure 11:
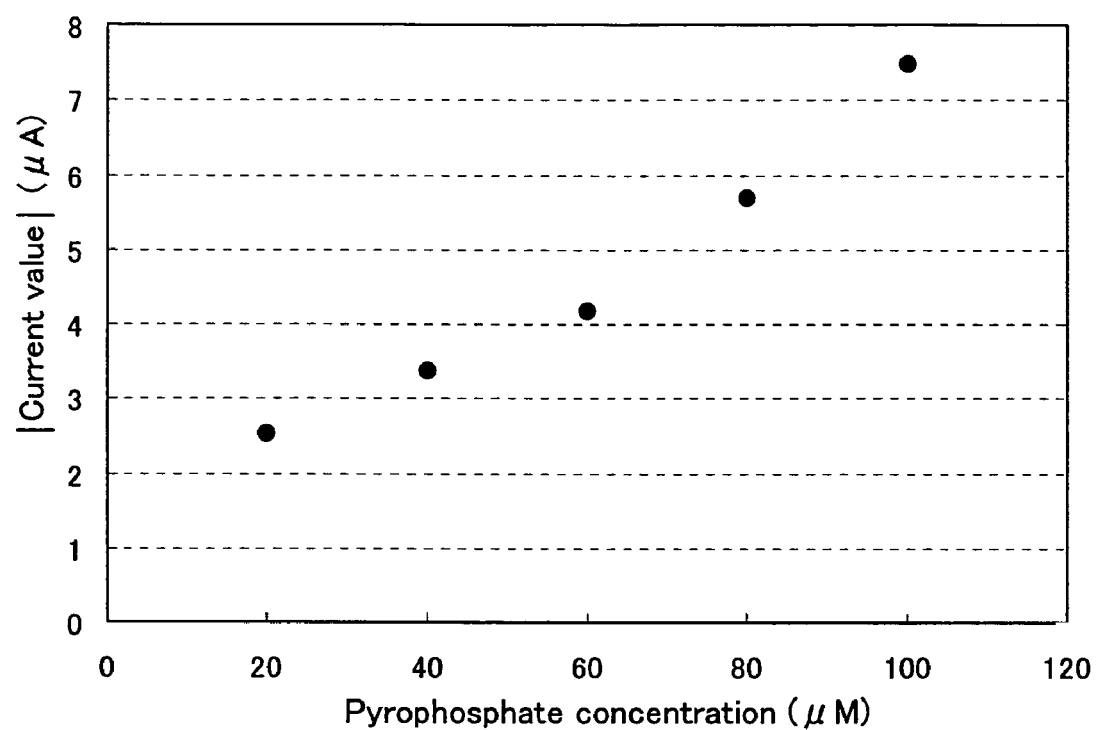
FIG. 11 is a graph showing a relationship between the concentration of pyrophosphate and the current value in Example 6.

Next, the current value after 100 seconds passed is illustrated in FIG. 11 when the amount of the pyrophosphate was varied. In FIG. 11, the absolute value of the current value (µA) is indicated by the longitudinal axis; final concentration of pyrophosphate (µM) is indicated by the horizontal axis; and the current value at each pyrophosphate concentration is depicted by a black circle. As shown in FIG. 11, the current value after 100 seconds passed exhibited a favorable linear relationship with the amount of pyrophosphate added.

When data shown in FIG. 11 obtained by this Example is compared with data shown in FIG. 8 obtained by Example 3, it is proven that a pyrophosphate is detected with higher sensitivity according to this Example. Therefore, detection of a pyrophosphate with higher sensitivity can be accomplished under the condition employed in this Example than the condition employed in Example 3.

According to the present invention, quantitative detection of an inorganic phosphoric acid in a sample with high sensitivity at a high speed is provided in which an electrochemical process is used. Furthermore, by converting a pyrophosphate into an inorganic phosphoric acid, quantitative measurement of the pyrophosphate with high sensitivity at a high speed is provided. Additionally, according to the present invention, by measuring a pyrophosphate which is produced concurrent with an extension reaction of a nucleic acid, presence of a targeted nucleic acid can be quantitatively measured. Furthermore, determination of a base in a SNP site of a targeted nucleic acid can be executed with high sensitivity at a high speed.

It will be obvious to those having skill in the art that many changes may be made in the above-described details of the preferred embodiments of the present invention. The scope of the present invention, therefore, should be determined by the following claims.

What is claimed is:

1. A method of detecting an inorganic phosphoric acid which comprises:
    subjecting a sample to a measurement system including glyceraldehyde-3-phosphate, oxidized nicotinamide adenine dinucleotide or oxidized nicotinamide adenine dinucleotide phosphate, glyceraldehyde phosphate dehydrogenase, diaphorase, and an electron mediator; and
    measuring a current value in said measurement system, wherein said current value indicates the concentration of the inorganic phosphoric acid in said sample, and the inorganic phosphoric acid is detected within 100 seconds after subjecting said sample to the measurement system.

2. The method of detecting an inorganic phosphoric acid according to claim 1 wherein said electron mediator is at least one selected from the group consisting of a ferricyanide, 1,2-naphthoquinone-4-sulfonate, 2,6-dichlorophenol indophenol, dimethylbenzoquinone, 1-methoxy-5-methylphenazinium sulfate, methylene blue, gallocyanine, thionine, phenazine methosulfate, and Meldola Blue.

3. The method of detecting an inorganic phosphoric acid according to claim 1 wherein said measurement system further comprises adenosine diphosphate and phosphoglycerate kinase.

4. A method of detecting a pyrophosphate which comprises:
    converting the pyrophosphate in a sample into an inorganic phosphoric acid;
    subjecting said sample to a measurement system including glyceraldehyde-3-phosphate, oxidized nicotinamide adenine dinucleotide or oxidized nicotinamide adenine dinucleotide phosphate, glyceraldehyde phosphate dehydrogenase, diaphorase, and an electron mediator; and
    measuring a current value in said measurement system, wherein said current value indicates the concentration of the pyrophosphate in said sample, and the pyrophosphate is detected within 100 seconds after subjecting said sample to the measurement system.

5. The method of detecting a pyrophosphate according to claim 4 wherein said conversion of the pyrophosphate into an inorganic phosphoric acid is conducted using pyrophosphatase.

6. A method of detecting a nucleic acid which comprises:
    subjecting a sample to a reaction system including a DNA probe having a complementary sequence to the sequence of said nucleic acid, DNA polymerase and a deoxynucleotide, and allowing extension of said DNA probe whereby a pyrophosphate produced concurrent with the extension reaction of said DNA probe;
    converting the pyrophosphate produced in the sample into an inorganic phosphoric acid;
    subjecting said sample to a measurement system including glyceraldehyde-3-phosphate, oxidized nicotinamide adenine dinucleotide or oxidized nicotinamide adenine dinucleotide phosphate, glyceraldehyde phosphate dehydrogenase, diaphorase, and an electron mediator; and
    measuring a current value in said measurement system, wherein said current value indicates the concentration of the nucleic acid having a specified sequence in said sample, and the nucleic acid is detected within 100 seconds after subjecting said sample to the measurement system.

7. The method of detecting a nucleic acid according to claim 6 wherein said extension reaction of the DNA probe is a PCR reaction.

8. A method of typing a SNP sequence of a DNA which comprises:
    subjecting a sample to a reaction system including a DNA probe having a complementary sequence to the sequence of said DNA and having a SNP site, DNA polymerase and a deoxynucleotide, and allowing extension of said DNA probe whereby a pyrophosphate produced concurrent with the extension reaction of said DNA probe;
    converting the pyrophosphate produced in the sample into an inorganic phosphoric acid;
    subjecting said sample to a measurement system including glyceraldehyde-3-phosphate, oxidized nicotinamide adenine dinucleotide or oxidized nicotinamide adenine dinucleotide phosphate, glyceraldehyde phosphate dehydrogenase, diaphorase, and an electron mediator; and
    measuring a current value in said measurement system, wherein said current value indicates the presence of the DNA having a specified sequence in said sample, and the SNP sequence of the DNA is typed within 100 seconds after subjecting said sample to the measurement system.

9. The method of typing a SNP sequence of a DNA according to claim 8 wherein said extension reaction of the DNA probe is a PCR reaction.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Chemically synthesized

<400> SEQUENCE: 1
gatgagttcg tgtccgtaca act                                    23

<210> SEQ ID NO 2
<211> LENGTH: 25
<212> TYPE: DNA
<213> ORGANISM: Artificial Sequence
<220> FEATURE:
<223> OTHER INFORMATION: Chemically synthesized

<400> SEQUENCE: 2
ggttatcgaa atcagccaca gcgcc                                  25

<210> SEQ ID NO 3
<211> LENGTH: 23
<212> TYPE: DNA
<213> ORGANISM: Artificial Sequence
<220> FEATURE:
<223> OTHER INFORMATION: Chemically synthesized

<400> SEQUENCE: 3
gatgagttcg tgtccgtaca aca                                    23
```